United States Patent
Krenn et al.

(10) Patent No.: US 6,994,973 B2
(45) Date of Patent: Feb. 7, 2006

(54) METHOD AND AGENT FOR DETERMINING TOTAL WATER HARDNESS

(75) Inventors: Karl-Dieter Krenn, Pfungstadt (DE); Dieter Tanzer, Ober-Ramstadt (DE)

(73) Assignee: Merck Patent GmbH, Darmstadt (DE)

( * ) Notice: Subject to any disclaimer, the term of this patent is extended or adjusted under 35 U.S.C. 154(b) by 135 days.

(21) Appl. No.: 10/433,839

(22) PCT Filed: Aug. 30, 2001

(86) PCT No.: PCT/EP01/09967

§ 371 (c)(1),
(2), (4) Date: Jun. 9, 2003

(87) PCT Pub. No.: WO02/46742

PCT Pub. Date: Jun. 13, 2002

(65) Prior Publication Data

US 2004/0033484 A1    Feb. 19, 2004

(30) Foreign Application Priority Data

Dec. 8, 2000   (DE) ............................... 100 61 140

(51) Int. Cl.
*C12Q 1/68* (2006.01)
(52) U.S. Cl. .......................................... 435/6
(58) Field of Classification Search ...................... 435/6
See application file for complete search history.

(56) References Cited

U.S. PATENT DOCUMENTS

| 3,822,116 | A | * | 7/1974 | Morin .......................... 436/74 |
| 3,938,954 | A | * | 2/1976 | Stavropoulos et al. ......... 436/74 |
| 4,871,678 | A | * | 10/1989 | Wahl et al. .................... 436/79 |
| 4,904,605 | A | * | 2/1990 | O'Brien et al. ............. 436/169 |
| 5,302,346 | A | * | 4/1994 | Vogel et al. ................... 422/56 |

FOREIGN PATENT DOCUMENTS

JP    62064951 A  *  3/1987

\* cited by examiner

*Primary Examiner*—Susan D. Coe
*Assistant Examiner*—S. B. McCormick-Ewoldt
(74) *Attorney, Agent, or Firm*—Millen, White, Zelano & Branigan, P.C.

(57) ABSTRACT

The invention relates to a dry chemical method and a test strip for determining calcium and magnesium in aqueous samples. Said test strip contains o-cresolphthalein complex (o-CPC; CAS Registry No. 2411-89-4) as a colour-causing reagent in a buffer system with a pH value of below 8.5. By using in particular an aqueous ethanolic imidazole buffer with a pH value of 6.75, conditions can be set up in such a way that the o-CPC has an identical molar sensitivity with respect to Ca and Mg. The total water hardness of aqueous samples can thus be easily determined.

8 Claims, No Drawings

METHOD AND AGENT FOR DETERMINING TOTAL WATER HARDNESS

The invention relates to a dry-chemical method and a test strip for the rapid, quantitative determination of calcium and magnesium in aqueous samples.

Naturally occurring water, including our drinking water, contains, besides various gases, a number of salts and other compounds which are dissolved out of the soil and rocks. Of particular importance here are the hardness components of water. The term total hardness is taken to mean the alkaline-earth metal ions dissolved in the water, which are essentially calcium (Ca) and magnesium (Mg) salts. Strontium and barium only occur in negligible traces. About 70–85% of the total hardness is attributable to the Ca content and about 15–30% to the Mg content of the water.

The hardness of water is specified in Germany in German degrees of hardness (° dH), with the hardness being calculated as CaO. 1° dH is defined as corresponding to a content of 10 mg of CaO/l or 0.178 mmol of CaO/l or 7.14 mg of MgO/l of water (for example K. Höll; Wasser [Water], 7th Edition (1986), Walter de Gruyter, Berlin).

Water having a hardness of 0–7° dH is known as soft (hardness range 1), that having a hardness of 8–14° dH is known as moderately hard (hardness range 2), that having a hardness of 15–20° dH is known as hard (hardness range 3), and that having a hardness of greater than 21° dH is known as very hard (hardness range 4).

Soft water is found in high-precipitation regions with low-solubility rocks, while hard water is found in particular in low-precipitation regions with gypsum or lime rocks. In addition, seasonal variations are not inconsiderable.

In many industrial and commercial processes, the water must have only low or zero hardness, and therefore the total hardness content must be checked regularly.

As the main quality criterion of the water, the water hardness influences the taste of food and drinks (for example coffee, wine, beer and mineral water). In addition, the effect of the water hardness on the health of humans is also under discussion. In general, excessively soft rather than excessively hard water is regarded as a health risk since it is more capable of mobilising heavy-metal traces, for example from pipelines, and has an adverse effect on bone and tooth formation.

The determination of the total hardness of water is therefore of considerable importance in food analysis and environmental analysis.

The total hardness is predominantly determined by titrimetric methods (titration). According to DIN 38409 Part 6, the total hardness is determined complexometrically using Titriplex® III solution (ethylenedinitrilotetraacetic acid disodium salt) against an indicator buffer tablet.

The calcium and magnesium content is also frequently determined by means of spectroscopic methods (for example atomic absorption, flame photometry) and the total hardness content calculated therefrom (for example L. A. Hütter, Wasser und Wasseruntersuchung [Water and Water Analysis], 4th Edition (1990), Verlag Sauerlander, Aarau).

Available methods for the rapid determination of total hardness are based on the titrimetric determination method. Owing to the determination accuracy, so-called wet-chemical test sets are usually employed for this purpose. In this method, an indicator is added to a measured-out amount of sample, and the titration agent is added or introduced dropwise by means of a suitable metering device (for example pipette). The amount of titration agent consumed is a measure of the total hardness of the sample and can be assigned, for example, via a scale on the pipette or via the number of drops.

Also known are wet-chemical methods for the determination of calcium and magnesium which are not based on a titrimetric method, but instead use the acid-base indicator orthocresolphthalein complexon (o-CPC: 3',3"-bis-[(bis(carboxymethyl)amino)methyl]-5',5'-dimethylphenolphthalein—also known as Phthalein Purple) as colouring reagent (indicator). In particular, this dye is used for the determination of Ca in body fluids.

Examples are given in DE 2335350, EP 0 203 334 and W. R. Moorehead and H. G. Biggs; Clin. Chem. 20 (1974), 1458–1460.

The disadvantage of these known methods is that they cannot be used for quantitative parallel determination of Ca and Mg.

In addition, the methods are inconvenient and do not meet the demands made by the customer for a simple determination method for total hardness, since total hardness determinations are frequently carried out by untrained personnel with no background in the area. For example, it is necessary to use reagent solutions which have to be disposed of in a suitable manner after the determination.

Analysis with solid, sorptive supports, so-called test sticks, has recently increased in importance. The main advantages of these dry-chemical methods include, in particular, simple handling and straightforward disposal owing to the small amounts of reagents. All or the majority of the reagents necessary for the determination reaction are embedded in corresponding layers of a solid, sorptive or swellable support, to which the sample is applied. After contact of the reaction zone with the sample, the determination reaction proceeds. The colour formed is a measure of the amount of analyte to be determined and can be assessed visually, i.e. semi-quantitatively, or quantitatively using simple reflectometers.

Test sticks for the determination of total hardness are commercially available. The determination is likewise based on the titrimetric methods already mentioned above. For the determination, the test sticks need only be dipped into the sample. A plurality of determination zones, which, besides other reagents necessary for the determination reaction, contain various amounts of titration agent (Titriplex® III), are applied to test sticks of this type. Depending on the hardness of the water to be analysed and the amount of titration agent, a defined colour change occurs on the test zones.

The main disadvantage of these test sticks is that, as a consequence of the determination principle, only the order of magnitude of the total hardness can be determined. This type of determination cannot be used for quantitative analysis with the aid of a reflectometer. This requires a continuous change of the colour depth on the test stick, i.e. a decrease or increase in remission at a certain wavelength.

In addition, the production of these test sticks is very complex since a plurality of zones impregnated with different amounts of reagents have to be sealed onto a support.

A further disadvantage of the known test stick determination for total hardness is, in particular, the difficulty in assigning the reaction zones to the colour scale, since the coloration formed on the test zones is not stable and increases continuously.

The existing determination principle is likewise unsuitable for the production of multiple test strips, in which a plurality of determination zones for different parameters have to be applied to a test strip. This form of test strips is used, in particular, in diagnostics and in the aquaristics area.

The present invention is therefore based on the object of providing a method for the determination of total hardness in aqueous samples which does not have the above disadvantages, can be carried out simply and rapidly, and is inexpensive. The method should also enable integration of total hardness into multiple test strips. In particular, the method should be accessible not only to semi-quantitative, visual, but also to quantitative evaluation using a reflectometer.

It has been found that a method for the determination of total hardness by means of a test strip containing orthocresolphthalein complexon as colouring reagent in a neutral to acidic buffer meets all the said requirements.

The present invention therefore relates to a method for the determination of calcium and magnesium in aqueous samples, characterised in that a test strip to which orthocresolphthalein complexon has been applied as colouring reagent in a buffer system having a pH of below 8.5 is wetted with the sample to be analysed, and the resultant colour reaction is evaluated reflectometrically or visually.

In a preferred embodiment, the pH of the buffer system is less than or equal to pH 7.

The present invention also relates to a test strip for the determination of Ca and Mg having at least one zone which contains at least orthocresolphthalein complexon in a buffer system of pH <8.5.

In a preferred embodiment, the buffer system consists of an imidazole buffer, pH 6.75.

In a preferred embodiment, at least one zone of the test strip additionally contains a barium salt.

In another preferred embodiment, at least one zone of the test strip contains a Ca- or Mg-specific or nonspecific complexing agent.

In a preferred embodiment, the test strip, in addition to at least one zone for the determination of Ca and Mg according to the invention, has further zones for the determination of other analytes, such as, for example, nitrite, nitrate, pH or carbonate hardness.

The present invention also relates to an analytical kit for the determination of Ca and Mg in aqueous samples which contains at least one test strip according to the invention.

The method according to the invention and the test strip according to the invention are particularly suitable for the determination of the total amount of Ca and Mg in aqueous samples, such as water samples, foods or body fluids. The method according to the invention is particularly preferably used for the analysis of water and food samples. In the case of food samples, it should be noted that a certain proportion of the Ca and/or Mg to be determined is frequently in bound form. In this case, the sample must first be digested in a suitable manner.

The basis of the method according to the invention is the use of the colouring reagent orthocresolphthalein complexon (o-CPC: 3',3"-bis[(bis(carboxymethyl)amino)methyl]-5',5'-dimethylphenolphthalein) in combination with a buffer of pH <8.5.

The determination system used in the method according to the invention is in the form of a test strip, i.e. an impregnated matrix, with all the reagents necessary for the determination (colouring reagent, buffer system, optionally also stabilisers and solubilisers) being embedded in a sorptive support located on the test strip. The sorptive support to which the determination reagents have been applied usually does not cover the entire test strip, but instead merely one zone of the test strip. In this way, it is possible not only to have one zone with a composition of determination reagents, but instead to combine a plurality of zones with different compositions, for example for the detection of different concentration ranges of an analyte or for the determination of different analytes, on one test strip. In accordance with the invention, the region of the test strip to which the reagents necessary for the determination of an analyte have been applied to a sorptive support is therefore known as a zone.

All known methods in which orthocresolphthalein complexon is employed as indicator use buffer systems which produce pH values above pH 9. It has been found that these basic buffer systems are unsuitable for use according to the invention on a test strip, since the alkaline conditions result, depending on the pH, in more or less intense inherent coloration without the presence of Ca and Mg (blank value). It has been found that, in the case of the use of test strips under alkaline reaction conditions (pH >8.5), the coloration of the blank value differs only insignificantly from the coloration of a sample with high contents of calcium and magnesium.

It has now been found that an essential prerequisite for achieving a low blank value using o-CPC is the setting of an at least weakly alkaline pH (<8.5), better an approximately neutral or even weakly acidic pH while simultaneously maintaining the requisite sensitivity to Ca and Mg.

For the determination of the sum of Ca and Mg, a further essential prerequisite is the establishment of conditions which result in precisely identical molar sensitivity for Mg and Ca.

The buffer system must therefore be such that on the one hand only a very low blank value, or none at all, occurs, and on the other hand a sufficiently high, identical molar sensitivity with respect to Ca and Mg results.

Suitable buffer systems for setting the pH are those which can be applied to a sorptive support, are compatible with the other constituents of the test and do not interfere with the determination reaction.

Particular preference is given to buffer systems based on amines, particularly preferably heterocyclic amines. Examples of particularly suitable buffer systems are imidazole, 1-methylimidazole, 2-methylimidazole, pyrazole, pyrimidine, pyridazine, piperazine, triazole and triazine buffers, or derivatives or mixtures thereof. Particular preference is given here to an imidazole buffer system. Suitable solvents, depending on the buffer system, are preferably mixtures of alcohols, typically branched or unbranched C1- to C6-alcohols, or of glycerol with water.

Particular preference is given to an aqueous-ethanolic imidazole buffer. The concentration of imidazole in the impregnation solution should be in the range 0.1–1.0 mmol/l, more preferably in the range 0.3–0.4 mmol/l. The water:ethanol ratio should be in the mixing ratio from 1:4 to 4:1. A ratio of 1:3 is particularly preferred.

The concentration of o-CPC in the buffer solution should be in the range 1–20 mmol/l, more preferably in the range 2–5 mmol/l.

By specifically setting the pH of the above buffer systems, it is possible to establish conditions under which o-CPC has an identical molar sensitivity to Ca and Mg. In the case of the preferred aqueous-ethanolic imidazole buffer, a pH of 6.75 should be set (see Example 3). A person skilled in the art is able to find suitable pH values for other buffer systems by determining the respective absorbance values.

On use of the buffer systems which are preferred in accordance with the invention, it has proven particularly advantageous that o-CPC does not, as described in the prior art, firstly have to be dissolved in a strongly acidic medium, but instead can be dissolved directly in the buffer solution.

An essential advantage for a test system is its long shelf life without change in the test properties (in particular calibration data). Stabilisers are therefore frequently integrated into a test system. The impregnation solution for the production of the test strip according to the invention may therefore optionally also contain a stabiliser. Stabilisers, such as, for example, alkylpolyalkylene glycol ethers, hydroxypropylcellulose or polyalcohols, are known to the person skilled in the art. A barium salt is particularly preferably added to the test strip according to the invention as stabiliser, since it has been found that the addition of traces of a barium salt (particularly preferably barium chloride) to the impregnation solution enables not only significant stabilisation of the test system (shelf life at room temperature >2 years), but also at the same time an improvement in the homogeneity of the coloration of the test zones. This has the consequence of higher determination accuracy and reproducibility of the determination. The concentration of barium salts, preferably barium chloride, in the impregnation solution should be in the range 0.05–1.0 mmol/l, more preferably in the range 0.1–0.2 mmol/l (see Example 1).

Incorporation of a suitable complexing agent into the test strip according to the invention and setting of a pH which is optimal for the particular element enable the determination system according to the invention also to be employed for the separate determination of Ca and Mg. The determination of a suitable pH and suitable complexing agents is known to the person skilled in the art. 8-Hydroxyquinoline and 8-hydroxyquinolinesulfonic acid have proven particularly advantageous for the complexing of Mg, and [bis(aminoethyl) glycol ether N,N,N',N'-tetraacetic acid (=Titriplex VI) has proven particularly advantageous for the complexing of Ca (see Examples 4 and 5).

In addition, incorporation of a complexing agent which is nonspecific with respect to Ca and Mg, such as, for example, Titriplex III (ethylenedinitrilotetraacetic acid disodium salt), into the determination system also enables the sensitivity of the determination to be influenced, i.e. the determination to be made less sensitive. Combination of two test zones of different sensitivity enables the measurement range of the test strip to be increased correspondingly. This is of major importance, in particular, for the determination of total hardness, since water can have very different hardness values (range about 0.5–30° dH), and a test system should cover this measurement range (see Example 2).

The sorptive supports used for the test strips according to the invention can be all materials which are usually used for dry-chemical tests of this type and are free from calcium and magnesium. The most widespread is the use of filter paper, but it is also possible to employ other sorptive cellulose or plastic products.

The sorptive supports are impregnated in a known manner with impregnation solutions, preferably the buffer system, which contain all reagents necessary for the determination of total hardness, calcium or magnesium. The impregnated and dried papers can be cut to size in a suitable manner and stuck or sealed onto support films in a known manner in order to produce the test strips.

In order to carry out the method according to the invention, a test strip containing at least one zone with o-CPC in a buffer of pH <8.5 is dipped briefly into the sample to be analysed or wetted with the sample to be analysed. Any excess sample solution is subsequently wiped off. Within a short time (usually <1 minute), a colour develops which remains stable over the analysis period and can be analysed visually or reflectometrically.

The method according to the invention and the test strips according to the invention are particularly suitable for use in analytical kits. An analytical kit according to the invention contains at least one test strip according to the invention. This is preferably at least one test strip for the determination of the total content of Ca and Mg in an aqueous sample. The analytical kit may optionally contain further constituents, such as, for example, a description of the performance of the method or a colour table for visual assessment.

The method according to the invention thus offers a simple, rapid and sensitive method for the determination of Mg and Ca in aqueous samples. The simple performance of the method enables the determination to be carried out even by untrained personnel without complex equipment and without handling toxic chemicals. Since only one, for covering a large concentration range usually two, determination zones are necessary on the test strip, even for a quantitative determination, the determination principle according to the invention can also be integrated into multiple test strips without difficulty. It can thus, for example, be combined with determination zones for nitrate, nitrite, pH and/or carbonate hardness.

Even without further details, it is assumed that a person skilled in the art will be able to utilise the above description in its broadest scope. The preferred embodiments and examples should therefore merely be regarded as descriptive disclosure which is absolutely not limiting in any way.

The complete disclosure content of all applications, patents and publications mentioned above and below, in particular the corresponding application DE 100 61 140, filed on Aug. 12, 2000, is incorporated into this application by way of reference.

EXAMPLES

Example 1

Determination of Total Hardness Using Test Strips—Reflectometric Evaluation of the Reaction Colour Production of the Test Sticks:

The following impregnation solution is applied to a filter paper (Binzer, 1450 CV; acid-washed) and then dried using warm air. The paper is sealed onto a white support film using hot-melt adhesive (for example adhesive Dynapol 1272) and cut into strips in a suitable manner so that a reaction zone measuring about 6 mm×8 mm results.

Composition of the Impregnation Solution:

0.3 g of o-CPC and 3.3 g of imidazole are weighed successively into 100 ml of absolute ethanol and dissolved with stirring. 30 ml of water and 1 ml of 0.1% barium chloride solution are subsequently added. The pH of the solution is adjusted to pH 6.75 using hydrochloric acid, 1 mol/l.

Preparation of the Standard Solutions:

Aqueous standard solutions are prepared by weighing-in a suitable calcium or magnesium salt, preferably calcium chloride dihydrate or magnesium nitrate hexahydrate.

Analysis:

For the determination, the test sticks are briefly dipped into the sample solution so that they are completely wetted.

Depending on the total hardness, violet colorations of different intensity which are stable over an extended period form within a few seconds. These can be evaluated visually after only 15 seconds by comparison with a colour card.

For quantitative evaluation, the test strips are evaluated after precisely 15 seconds in a small manual diode-based reflectometer (RQflex® reflectometer). The correlation between the measured relative remission (%) and the total hardness is shown by Table 1.

TABLE 1

| °dH | % rem |
|---|---|
| 0 | 70 |
| 1.4 | 62 |
| 1.8 | 58 |
| 4.2 | 53 |
| 5.6 | 49 |
| 7.0 | 45 |
| 8.4 | 41 |
| 9.8 | 37 |
| 12.6 | 30 |

Example 2

Combination of Two Reaction Zones of Different Determination Sensitivity in Order to Increase the Measurement Range Using the Example of Total Hardness An additional zone impregnated with the following reagent solution was applied to the test sticks from Example 1. The separation of the two test zones measuring 8×6 mm was 4 mm.

Composition of the Impregnation Solution for Zone 2:

2.2 ml of a 0.1 molar Titriplex III solution (ethylenedinitrilotetraacetic acid disodium salt) are added to 70 ml of the impregnation solution for zone 1 (see Example 1). The pH of the solution is adjusted to pH 6.75 using hydrochloric acid, 1 mol/l.

Analysis:

The test strips were measured as described under Example 1 after precisely 15 seconds in the RQflex® reflectometer. The RQflex® reflectometer has the double beam optics necessary for this type of evaluation.

The correlation between the measured relative remission (%) and the total hardness for the two zones is shown by Table 2.

TABLE 2

| °dH | Zone 1 [% rem] | °dH | Zone 2 [% rem.] |
|---|---|---|---|
| 0 | 70 | 11.2 | 64 |
| 1.4 | 62 | 12.6 | 59 |
| 1.8 | 58 | 14.0 | 53 |
| 4.2 | 53 | 15.4 | 48 |
| 5.6 | 49 | 17.5 | 42 |
| 7.0 | 45 | 21.0 | 36 |
| 8.4 | 41 | 25.2 | 30 |
| 9.8 | 37 | 28.0 | 27 |
| 12.6 | 30 | 30.0 | 26 |

Combination of the two test zones enables the total hardness to be determined quantitatively in the range about 0.1–30° dH.

Example 3

Effect of pH of the Impregnation Solution on the Determination Sensitivity of the System to Ca and Mg The impregnation solution from Example 1 was adjusted to various pH values (pH 6.75 and 7.1) using HCl, and test sticks were produced correspondingly. Ca standards and Mg standards of the same molarity were subsequently measured.

The correlation between the measured relative remission (%) and the Ca or Mg concentration as a function of the pH of the impregnation solution is shown by Tables 3 and 4.

The same molar sensitivity for Ca and Mg was only obtained at a pH of the impregnation solution of 6.75, which is the prerequisite for the determination of the sum of Ca and Mg.

TABLE 3

Impregnation solution of pH 6.75

| mmol/l Ca or Mg | Corresponds to mg/l Ca | Corresponds to mg/l Mg | Ca [% rem.] | Mg [% rem.] |
|---|---|---|---|---|
| 0 | 0 | 0 | 69.5 | 69.5 |
| 0.25 | 10 | 6 | 63.0 | 62.2 |
| 0.5 | 20 | 12 | 55.8 | 55.3 |
| 1.25 | 50 | 30 | 44.1 | 43.4 |
| 2.5 | 100 | 60 | 29.5 | 28.4 |
| 3.75 | 150 | 90 | 23.9 | 22.8 |
| 5.0 | 200 | 120 | 20.4 | 20.0 |

TABLE 4

Impregnation solution of pH 7.1

| mmol/l Ca or Mg | Corresponds to mg/l Ca | Corresponds to mg/l Mg | Ca [% rem.] | Mg [% rem.] |
|---|---|---|---|---|
| 0 | | | 69.0 | 68.5 |
| 0.5 | 20 | 12 | 48.5 | 53.9 |
| 1.25 | 50 | 30 | 26.3 | 32.6 |
| 2.5 | 100 | 60 | 16.2 | 21.3 |
| 3.75 | 150 | 90 | 13.8 | 18.4 |

Example 4

Determination of Magnesium Using Test Strips—Reflectometric Evaluation of the Reaction Colour Titriplex VI was added to the impregnation solution from Example 1 in order to complex calcium. The concentration of Titriplex VI in the impregnation solution was 7.5 g/l. The pH of the solution was set to 7.0 using HCl. The addition of Titriplex VI enables interference-free analysis of Mg in the presence of up to 200 mg/l of Ca.

The correlation between the measured relative remission (%) and the magnesium content is shown by Table 5.

TABLE 5

| mg/l Mg | % rem. |
|---|---|
| 0 | 68 |
| 5 | 60 |
| 10 | 54 |
| 25 | 43 |

TABLE 5-continued

| mg/l Mg | % rem. |
|---------|--------|
| 50      | 33     |
| 75      | 26     |

Example 5

Determination of Calcium Using Test Strips—Reflectometric Evaluation of the Reaction Colour 8-Hydroxyquinoline-5-sulfonic acid was added to the impregnation solution from Example 1 in order to complex magnesium. The concentration of 8-hydroxyquinoline-5-sulfonic acid in the impregnation solution was 11.8 g/l. The pH of the solution was set to 7.4 using HCl. The addition of Titriplex VI enables interference-free analysis of Ca in the presence of up to 100 mg/l of Mg.

The correlation between the measured relative remission (%) and the calcium content is shown by Table 6.

TABLE 6

| mg/l Ca | % rem. |
|---------|--------|
| 0       | 70     |
| 10      | 65     |
| 25      | 54     |
| 50      | 47     |
| 75      | 40     |
| 100     | 31     |

Example 6

Practical Test: Determination of Total Hardness, Calcium and Magnesium in Water Samples—Comparison with Standard Methods 30 drinking-water samples from the public supply network of various communities in Lower Saxony were employed for the analysis.

The standard method employed for the determination of Mg was atomic absorption spectroscopy (see Table 7) and that employed for the determination of Ca was flame photometry (see Table 8). The total hardness (see Table 9) was calculated from the individual values for calcium and magnesium. The total hardness was determined titrimetrically. In accordance with DIN 38409 Part 6, the total hardness was determined complexometrically using Titriplex® III solution (ethylenedinitrilotetraacetic acid disodium salt) against an indicator buffer tablet (see Table 9).

The test sticks described in the preceding examples were employed for the reflectometric analyses: the test sticks from Example 2 (see Table 9) for the determination of total hardness, the test sticks from Example 4 (see Table 7) for the determination of magnesium, and those from Example 5 (see Table 8) for the determination of calcium.

TABLE 7

Determination of Mg ions in drinking-water samples (mg/l)
Comparison between AAS and test sticks with refl. evaluation

| Sample | AAS | Test sticks |
|--------|-----|-------------|
| 1      | 10  | 7           |
| 2      | 10  | 6           |
| 3      | 5   | <5          |
| 4      | 38  | 40          |
| 5      | 10  | 7           |
| 6      | 9   | 5           |
| 7      | 4   | <5          |
| 8      | 35  | 35          |
| 9      | 5   | 3           |
| 10     | 33  | 30          |
| 11     | 5   | <5          |
| 12     | 38  | 38          |
| 13     | 30  | 29          |
| 14     | 35  | 35          |
| 15     | 46  | 44          |
| 16     | 34  | 38          |
| 17     | 35  | 33          |
| 18     | 19  | 16          |
| 19     | 10  | 9           |
| 20     | 7   | 7           |
| 21     | 7   | <5          |
| 22     | 5   | <5          |
| 23     | 28  | 28          |
| 24     | 17  | 16          |
| 25     | 5   | <5          |
| 26     | 40  | 39          |
| 27     | 5   | <5          |
| 28     | 6   | <5          |
| 29     | 5   | <5          |
| 30     | 9   | <5          |

TABLE 8

Determination of Ca ions in drinking-water samples (mg/l)
Comparison between flame photometry and test sticks with reflectometric evaluation

| Sample | Flame photometry | Test sticks |
|--------|------------------|-------------|
| 1      | 77               | 71          |
| 2      | 158              | 124         |
| 3      | 50               | 41          |
| 4      | 112              | 105         |
| 5      | 95               | 89          |
| 6      | 62               | 54          |
| 7      | 62               | 54          |
| 8      | 83               | 87          |
| 9      | 72               | 73          |
| 10     | 95               | 101         |
| 11     | 99               | 100         |
| 12     | 84               | 88          |
| 13     | 73               | 79          |
| 14     | 77               | 78          |
| 15     | 128              | 109         |
| 16     | 57               | 54          |
| 17     | 77               | 79          |
| 18     | 150              | 124         |
| 19     | 48               | 49          |
| 20     | 23               | 18          |
| 21     | 43               | 39          |
| 22     | 40               | 48          |
| 23     | 97               | 102         |
| 24     | 77               | 79          |
| 25     | 39               | 34          |
| 26     | 114              | 112         |
| 27     | 45               | 40          |
| 28     | 44               | 40          |
| 29     | 41               | 40          |
| 30     | 43               | 44          |

TABLE 9

Titrimetric and reflectometric (using test sticks) determination of total hardness (° dH) in drinking-water samples and calculated values from the Ca and Mg determinations

| Sample | Titrimetric analysis | Test sticks | Calculated |
|---|---|---|---|
| 1 | 12.4 | 13.0 | 13.1 |
| 2 | 22.7 | 23.0 | 24.4 |
| 3 | 7.5 | 9.0 | 8.2 |
| 4 | 22.9 | 22.8 | 24.5 |
| 5 | 14.7 | 14.4 | 15.6 |
| 6 | 10.1 | 10.6 | 10.8 |
| 7 | 9.2 | 10.6 | 9.6 |
| 8 | 18.6 | 18.8 | 19.7 |
| 9 | 11.1 | 12.1 | 11.3 |
| 10 | 20.1 | 19.8 | 20.9 |
| 11 | 14.7 | 14.5 | 15.1 |
| 12 | 20.2 | 19.5 | 20.6 |
| 13 | 16.6 | 16.7 | 17.1 |
| 14 | 18.4 | 17.7 | 18.9 |
| 15 | 26.5 | 25.3 | 28.5 |
| 16 | 15.5 | 14.9 | 15.8 |
| 17 | 18.4 | 19.3 | 18.9 |
| 18 | 23.7 | 23.7 | 25.4 |
| 19 | 8.9 | 9.7 | 9.0 |
| 20 | 4.7 | 5.3 | 4.8 |
| 21 | 7.1 | 7.1 | 7.6 |
| 22 | 6.3 | 6.9 | 6.8 |
| 23 | 18.9 | 18.7 | 20.1 |
| 24 | 13.9 | 13.9 | 14.7 |
| 25 | 6.2 | 6.3 | 6.7 |
| 26 | 23.8 | 23.9 | 25.2 |
| 27 | 7.0 | 7.5 | 7.5 |
| 28 | 6.9 | 6.3 | 7.6 |
| 29 | 6.5 | 7.1 | 7.1 |
| 30 | 6.9 | 8.0 | 7.6 |

The invention claimed is:

1. A method for determining the presence of calcium and/or magnesium in an aqueous sample, comprising wetting with the sample a test strip to which orthocresolphthalein complexone has been applied as colouring reagent in a buffer system having a pH of below or equal to 7 and evaluating the resultant colour of the test strip reflectometrically or visually.

2. A test strip for the determination of the presence of calcium and/or magnesium in an aqueous sample, comprising at least one zone which contains at least orthocresolphthalein complexone in a buffer system having a pH of below or equal to 6.

3. A test strip according to claim 2, wherein the buffer system contains an imidazole buffer, pH 6.75.

4. A test strip according to claim 2, wherein at least one zone of the test strip contains a barium salt.

5. A test strip according to claim 2, wherein at least one zone of the test strip contains a Ca- or Mg-specific or nonspecific complexing agent.

6. A test strip according to claim 2, wherein the test strip has at least one zone for the determination of one or more other analytes than calcium and/or magnesium.

7. An analytical kit for the determination of Ca and/or Mg in aqueous samples which contains at least one test strip of claim 2.

8. A method according to claim 1, wherein the resultant colour of the test strip represents a quantitative amount of calcium and/or magnesium.

* * * * *

UNITED STATES PATENT AND TRADEMARK OFFICE
CERTIFICATE OF CORRECTION

PATENT NO. : 6,994,973 B2
APPLICATION NO. : 10/433839
DATED : February 7, 2006
INVENTOR(S) : Karl-Dieter Krenn et al.

It is certified that error appears in the above-identified patent and that said Letters Patent is hereby corrected as shown below:

Column 12, line 14 reads "equal to 6." should read --equal to 7.--

Signed and Sealed this

Twenty-fifth Day of July, 2006

JON W. DUDAS
*Director of the United States Patent and Trademark Office*